(12) United States Patent
Reich et al.

(10) Patent No.: US 7,320,962 B2
(45) Date of Patent: *Jan. 22, 2008

(54) HEMOACTIVE COMPOSITIONS AND METHODS FOR THEIR MANUFACTURE AND USE

(75) Inventors: Cary J. Reich, Sierra Madre, CA (US); A. Edward Osawa, San Francisco, CA (US); Helen Tran, San Jose, CA (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 286 days.

This patent is subject to a terminal disclaimer.

(21) Appl. No.: 10/761,922

(22) Filed: Jan. 20, 2004

(65) Prior Publication Data
US 2004/0214770 A1    Oct. 28, 2004

Related U.S. Application Data

(63) Continuation-in-part of application No. 09/553,969, filed on Apr. 21, 2000, and a continuation-in-part of application No. 09/330,315, filed on Jun. 10, 1999, now Pat. No. 6,706,690, which is a continuation of application No. 09/032,370, filed on Feb. 27, 1998, now Pat. No. 6,066,325, which is a continuation-in-part of application No. 08/903,674, filed on Jul. 31, 1997, now Pat. No. 6,063,061, and a continuation-in-part of application No. 08/704,852, filed on Aug. 27, 1996, now abandoned.

(60) Provisional application No. 60/050,437, filed on Jun. 18, 1997.

(51) Int. Cl.
A61K 38/17   (2006.01)
A61K 31/74   (2006.01)
A61K 35/14   (2006.01)
A61K 9/00    (2006.01)

(52) U.S. Cl. .......................... 514/21; 514/54; 514/60; 514/777; 514/944; 530/354; 530/356; 530/380; 530/402; 424/78.02; 424/78.06; 424/478; 435/810

(58) Field of Classification Search ................. 514/21, 514/54, 60, 777, 944; 530/354, 356, 362, 530/380, 402; 424/78.02, 78.06, 478; 435/810
See application file for complete search history.

(56) References Cited

U.S. PATENT DOCUMENTS

| 4,265,233 A | 5/1981 | Sugitachi et al. |
|---|---|---|
| 4,291,013 A | 9/1981 | Wahlig et al. |
| 4,300,494 A | 11/1981 | Graiff et al. |
| 4,347,234 A | 8/1982 | Wahling et al. |
| 4,424,208 A | 1/1984 | Wallace et al. |
| 4,536,387 A | 8/1985 | Sakamoto et al. |
| 4,655,211 A | 4/1987 | Sakamoto et al. |
| 4,803,075 A | 2/1989 | Wallace et al. |
| 4,891,359 A | 1/1990 | Saferstein et al. |
| 4,925,677 A | 5/1990 | Feijen |
| 4,946,870 A | 8/1990 | Partain, II et al. |
| 5,165,938 A | 11/1992 | Knighton |
| 5,178,883 A | 1/1993 | Knighton |
| 5,196,185 A | 3/1993 | Silver et al. |
| 5,204,382 A | 4/1993 | Wallace et al. |
| 5,292,362 A | 3/1994 | Bass et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,428,024 A | 6/1995 | Chu et al. |
| 5,516,532 A | 5/1996 | Atala et al. |
| 5,595,735 A | 1/1997 | Saferstein et al. |
| 5,648,506 A | 7/1997 | Desai et al. |
| 5,672,336 A | 9/1997 | Sharma |
| 6,066,325 A | 5/2000 | Wallace et al. |
| 6,110,484 A | 8/2000 | Sierra |

(Continued)

FOREIGN PATENT DOCUMENTS

WO    WO96/06883    3/1996

(Continued)

OTHER PUBLICATIONS

Ansell et al., "Gelfoam and autologous clot embolization: Effect on coagulation" *Invest. Radiol.* (1978) 13:115-120.

(Continued)

*Primary Examiner*—Jon Weber
*Assistant Examiner*—Abdel A. Mohamed
(74) *Attorney, Agent, or Firm*—Townsend and Townsend and Crew LLP (57) ABSTRACT

Dried hemoactive materials comprise both a cross-linked biologically compatible polymer and a non-cross-linked biologically compatible polymer. The cross-linked polymer is selected to form a hydrogel when exposed to blood. The non-cross-linked polymer is chosen to solubilize relatively rapidly when exposed to blood. The non-cross-linked polymer serves as a binder for holding the materials in desired geometries, such as sheets, pellets, plugs, or the like. Usually, the cross-linked polymer will be present in a particulate or fragmented form. The materials are particularly suitable for hemostasis and drug delivery.

29 Claims, 2 Drawing Sheets

U.S. PATENT DOCUMENTS

| | | | |
|---|---|---|---|
| 6,277,394 B1 | 8/2001 | Sierra | |
| 6,706,690 B2 * | 3/2004 | Reich et al. | 514/21 |

FOREIGN PATENT DOCUMENTS

| | | |
|---|---|---|
| WO | WO96/10374 | 4/1996 |
| WO | WO96/10428 | 4/1996 |
| WO | WO96/39159 | 12/1996 |
| WO | WO98/08550 | 3/1998 |

OTHER PUBLICATIONS

Barton et al., "Fibrin glue as a biologic vascular patch—a comparative study" (abstract posted at http://www.ncbi.nlm.nih.gov/ on Jan. 3, 2001 from) *J. Surg. Res.* (1986) 40(5):510-513.

Bruck, S.D., Ed., "Controlled Drug Delivery", CRC Press, Boca Raton, FL (1983) (title page and table of contents).

Cantor et al., "Gelfoam and thrombin in gastrointestinal bleeding: An experimental study" pp. 890-893.

Cantor et al., "Gelfoam and thrombin in treatment of massive gastroduodenal hemorrhage: A preliminary report" *Am. J. Surg.* (1950) pp. 883-887.

Cantor et al., "Gelfoam and thrombin in treatment of massive upper gastrointestinal hemorrhage" *Am. J. Surg.* (1951) pp. 230-235.

Chuang et al. "Sheath needle for liver biopsy in high-risk patients" *Radiology* (1988) 166:261-262.

Collins et al., "Enemata of gelfoam-milk suspension combined with thrombin solution to control massive hemorrhage following anorectal surgery" *Am. J. Proctol.* (1951) 2:60-63.

Edgerton et al., "Vascular hamartomas and hemangiomas: Classification and treatment" *Southern Med. J.* (1982) 75(12):1541-1547.

Heller et al., "Release of norethindrone from poly(ortho esters)" Polymer Engineering Scien. (1981) 21(11):727-731.

Hotz et al. "Collagen and fibrin as biologic binders for granular hydroxyapatite" (abstract posted at http://www.ncbi.nlm.nih.gov/ on Jan. 3, 2001 from) *Dtsch. Z. Mund. Kiefer Gesichstshir.* (1989) 13(4):296-300.

Jeong et al., "Biodegradable block copolymers as injectable drug-delivery systems" Nature (1997) 388:860-862.

Krill et al., "Topical thrombin and powdered Gelfoam: An efficient hemostatic treatment for surgery" *J. Tenn. Dent. Assoc.* (1986) 66(2):26-27.

Langer et al., "Chemical and physical structure of polymers as carriers for controlled release of bioactive agents: A review" Rev. Macro. Chem. Phys. (1983) C23(1):61-126.

Leong et al., "Polyanhydrides for controlled release of bioactive agents" Biomaterials (1986) 7:364-371.

Leong et al., "Polymeric controlled drug delivery" Adv. Drug Delivery Review (1987) 1:199-233.

Maok, "Hemostatic Agents" (1991) *Today's O.R. Nurse*, pp. 6-10.

Masal et al., "Synthesis of polyurethanes and investigation of other hydrolytic stability" Journal of Polymer Science, Polymer Symposium (1979) 66:259-268.

McClure et al., "Massive gastroduodenal hemorhage: Treatment with powered Gelfoam and buffered thrombin solution" *Surg.* (1952) 32:630-637.

Pitt et al., "Biodegradable drug delivery systems based on aliphatic polyesters: Application to contraceptives and narcotic antagonists" Controlled Release of Bioactive Materials, Baker, R., Ed., Academic Press, New York (1980) pp. 19-43.

Riley et al., "Percutaneous liver biopsy with plugging of needle track: A safe method for use in patients with impaired coagulation" *Lancet* (Aug. 25, 1984) pp. 436.

Sidman et al., "Biodegradable, implantable sustained release systems based on glutamic acid copolymers" Journal of Membrane Science (1979) 7:227-291.

Sugitachi et al. "Preoperative transcatheter arterial chemo-embolization for locally advanced breast cancer. Application for new thrombotic materials" *Japan J. Surg.* (1983) 13(5):456-458.

Sugitachi et al., "A newly devised chemo-embolic agent, G.T. XIII-ADM." (English abstract posted at http://www.ncbi.nlm.nih.gov/ on Jan. 3, 2001 from) *Gan. To. Kagaku Ryoho.* (1985) 12(10) 1942-1943.

Sugitachi et al., "Locoregional therapy in patients with malignant pleural effusion—two different types of BAC therapy" (English abstract posted at http://www.ncbi.nlm.nih.gov/ on Jan. 3, 2001 from) *Gan. To. Kagaku Ryoho.* (1992) 19(10):1640-1643.

Tobin et al., "Plugged liver biopsy in patients with impaired coagulation" (1989) *Digestive Diseases and Science* (1989) 34(1):13-15.

Tucker et al., *Absorbable Gelatin (Gelfoam) Sponge*, Charles C. Thomas, Publisher, Springfield, Illinois, 3-125.

Vander Salm et al., "Reduction of sternal infection by application of topical vancomycin" *J. Thorac. Surg.* (1989) 98:618-622.

Yuki et al., "Effects of endoscopic variceal sclerotherapy using GT XIII on blood coagulation tests and the renal kallikrein-kinin system" (English abstract posted as http://www.ncbi.nlm.nih.gov/ on Jan. 2, 2001 from) *Gastroentrol. Japan* (1990) 25(5):561-567.

Zins et al., "US-guided percutaneous liver biopsy with plugging of the needle track: A prospective study in 72 high-risk patients" *Radiology* (1992) 184(3):841-843.

\* cited by examiner

HEMOACTIVE COMPOSITIONS AND METHODS FOR THEIR MANUFACTURE AND USE

CROSS-REFERENCES TO RELATED APPLICATIONS

The present application is continuation-in-part of application Ser. No. 09/330,315, filed Jun. 10, 1999 (U.S. Pat. No. 6,706,690, Issued Mar. 16, 2004), and is also a continuation-in-part of application Ser. No. 09/553,969, filed Apr. 21, 2000, which was continuation of application Ser. No. 09/032,370, filed Feb. 27, 1998 (U.S. Pat. No. 6,066,325, Issued May 23, 2000), which was a continuation-in-part of application Ser. No. 08/903,674, filed on Jul. 31, 1997 (U.S. Pat. No. 6,063,061, Issued May 16, 2000), which was a continuation-in-part of provisional Application No. 60/050,437, filed on Jun. 18, 1997, and was a continuation-in-part of application Ser. No. 08/704,852, filed on Aug. 27, 1996 (Abandoned). The full disclosures of each of these applications are incorporated herein by reference.

BACKGROUND OF THE INVENTION

1. Filed of the Invention

The present invention relates generally to biocompatible polymeric compositions and methods for their production and use. More particularly, the present invention relates to compositions for promoting hemostasis and delivery of bioactive substances.

The ability to inhibit bleeding in a patient (hemostasis) and deliver bioactive substances to the patient (drug delivery) are both of great medical importance. Over the years numerous devices, compositions, and biological agents have been developed for both purposes. As no one device, composition, or approach can fulfill all medical needs, there continues to be a need to provide alternative and improved modalities for achieving both hemostasis and drug delivery.

In particular, it would be desirable to provide new and alternative compositions which are suitable for performing either or both hemostasis and drug delivery to patients. Preferably, such compositions should be a convenient matrix for topical delivery to surgical and/or traumatic wounds to a patient's tissue structures or skin. In particular, such compositions should be dry, be capable of storage for prolonged periods, be in a sheet or other easily manipulable form to facilitate placement, require minimum preparation by a user prior to use, be relatively easy to fabricate, be compatible with the delivery of a wide variety of biological and other active agents, and the like. In the case of hemostatic materials, it would be particularly advantageous to be able to remove excess material without causing further bleeding or other adverse events.

At least some of these objectives will be meet by the embodiments of the invention described hereinafter.

2. Description of the Background Art

Biodegradable injectable drug delivery polymers are described in U.S. Pat. No. 5,384,333 and by Jeong et al. (1997) "Nature," 388:860–862. Biodegradable hydrogels for controlled released drug delivery are described in U.S. Pat. No. 4,925,677. Resorbable collagen-based drug delivery systems are described in U.S. Pat. Nos. 4,347,234 and 4,291,013.

Aminopolysaccharide-based biocompatible films for drug delivery are described in U.S. Pat. Nos. 5,300,494 and 4,946,870. Water soluble carriers for the delivery of taxol are described in U.S. Pat. No. 5,648,506.

Polymers have been used as carriers of therapeutic agents to effect a localized and sustained release (Langer, et al., Rev. Macro. Chem. Phys., C23(1), 61, 1983; Controlled Drug Delivery, Vol. I and II, Bruck, S. D., (ed.), CRC Press, Boca Raton, Fla., 1983; Leong et al., Adv. Drug Delivery Review, 1:199, 1987). These therapeutic agent delivery systems simulate infusion and offer the potential of enhanced therapeutic efficacy and reduced systemic toxicity.

Other classes of synthetic polymers which have been proposed for controlled release drug delivery include polyesters (Pitt, et al., in Controlled Release of Bioactive Materials, R. Baker, Ed., Academic Press, New York, 1980); polyamides (Sidman, et al., Journal of Membrane Science, 7:227, 1979); polyurethanes (Maser, et al., Journal of Polymer Science, Polymer Symposium, 66:259, 1979); polyorthoesters (Heller, et al., Polymer Engineering Scient, 21:727, 1981); and polyanhydrides (Leong, et al., Biomaterials, 7:364, 1986). U.S. Pat. No. 5,595,735 describes a thrombin paste composition using polyethylene glycols as carriers.

Collagen-containing compositions which have been mechanically disrupted to alter their physical properties are described in U.S. Pat. Nos. 5,428,024; 5,352,715; and 5,204,382. These patents generally relate to fibrillar and insoluble collagens. An injectable collagen composition is described in U.S. Pat. No. 4,803,075. An injectable bone/cartilage composition is described in U.S. Pat. No. 5,516,532. A collagen-based delivery matrix comprising dry particles in the size range from 5 μm to 850 μm which may be suspended in water and which has a particular surface charge density is described in WO 96/39159. A collagen preparation having a particle size from 1 μm to 50 μm useful as an aerosol spray to form a wound dressing is described in U.S. Pat. No. 5,196,185. Other patents describing collagen compositions include U.S. Pat. Nos. 5,672,336 and 5,356,614.

A polymeric, non-erodible hydrogel that may be cross-linked and injected via a syringe is described in WO 96/06883.

The following pending applications, assigned to the assignee of the present application, contain related subject matter: U.S. Ser. No. 09/032,370, filed on Feb. 27, 1998; U.S. Ser. No. 08/903,674, filed on Jul. 31, 1997; U.S. Ser. No. 60/050,437, filed on Jun. 18, 1997; U.S. Ser. No. 08/704,852, filed on Aug. 27, 1996; U.S. Ser. No. 08/673,710, filed Jun. 19, 1996; U.S. Ser. No. 60/011,898, filed Feb. 20, 1996; U.S. Ser. No. 60/006,321, filed on Nov. 7, 1996; U.S. Ser. No. 60/006,322, filed on Nov. 7, 1996; U.S. Ser. No. 60/006,324, filed on Nov. 7, 1996; and U.S. Ser. No. 08/481,712, filed on Jun. 7, 1995. The full disclosures of each of these applications is incorporated herein by reference. WO 98/08550, which claims priority from U.S. Ser. No. 08/903,674, described cross-linked biological polymers which are useful as a component of the materials of the present invention.

SUMMARY OF THE INVENTION

According to the present invention, hemoactive materials comprise a dried, cross-linked biologically compatible polymer which forms a hydrogel when exposed to blood and a non-cross-linked biologically compatible polymer which solubilizes when exposed to blood. A cross-linked polymer is dispersed in a dried matrix of the non-cross-linked polymer, and the materials are delivered to surgical sites, wounds, and other target regions in tissue which are subject to bleeding or otherwise have blood present. By "hemoactive," it is meant that the compositions will interact in some way with blood when exposed to blood. At a minimum, the non-cross-linked biocompatible polymer will solubilize in the presence of blood and release the cross-linked biologically compatible polymer so that it can hydrate and form a gel as it absorbs water from the blood. Thus, the non-cross-linked biologically compatible polymer forms a binder which maintains the cross-linked polymer in a desirable form prior to use. Usually, the compositions will be in the form of a sheet, typically having a thickness in the range from 1 mm to 25 mm, preferably from 2 mm to 15 mm. Alternatively, the materials can be formed into powders, pellets, large blocks, plugs, cylinders, tubes, split tubes, or other forms which may be conveniently delivered or placed to target tissue sites. Additionally, the "hemoactive" materials may include other bioactive agents capable of providing desirable bioactivities. Of particular interest, the hemoactive materials may include hemostatic agents, such as blood clotting agents, e.g., thrombin, which will promote hemostatic activity of the material. A wide variety of other bioactive agents may be delivered, including other proteins, carbohydrates, nucleic acids, inorganic and organic biologically active molecules such as enzymes, enzyme inhibitors, antibiotics, anti-neoplastic agents, bacteriostatic agents, bactericidal agents, antiviral agents, anesthetics, anti-inflammatory agents, hormones, anti-angiogenic agents, antibodies, neurotransmitters, and the like. Additional components may be provided in the compositions, such as buffering agents, antioxidants, preservatives, viscosity modifiers, solubility modifiers, and the like, in order to enhance or modify the properties or shelf-life of the material. Preferably, the materials will be sterilized and maintained in a sterile package. Conventional sterilization methods include γ-irradiation, exposure to ethylene oxide, electronic beam irradiation, aseptic processing, and the like.

The compositions of the present invention will preferably comprise cross-linked biologically compatible polymers which are relatively persistent, usually having a degradation time of at least 1 day, preferably having a degradation time in the range from 2 days to 60 days. Conversely, the non-cross-linked biologically compatible polymers which form the binder will have a very short life and will typically dissolve in blood or aqueous media at physiologic temperature (37° C.) in less than 15 minutes, preferably in from 30 seconds to 10 minutes. Preferred cross-linked polymers will be fragmented, i.e., be present in the materials as discrete dry particles which, upon subsequent hydration, will have a size in the range from 0.01 mm to 5 mm, preferably from 0.05 mm to 1 mm. The cross-linked polymers will be swellable, and will have an equilibrium swell when fully hydrated in the range from 200% to 5,000%, preferably from 500% to 1000%.

Equilibrium swell, expressed as a percentage, is defined as the ratio of the difference between the equilibrium wet weight and dry weight of the cross-linked polymer and the dry weight of the polymer as follows:

$$\text{Equilibrium Swell (\%)} = \frac{\text{Wet Weight} - \text{Dry Weight}}{\text{Dry Weight}} \times 100$$

The equilibrium wet weight is measured after the polymer has had an extended period of time in contact with the wetting agent after which the polymer can no longer take up significant additional wetting agent. For example, a cross-linked polymer that takes up five times its dry weight in water at equilibrium is said to have an equilibrium swell of 500% in water. A cross-linked polymer that takes up no water (that is, its equilibrium wet weight is the same as its dry weight) is said to have an equilibrium swell of 0% in water.

The cross-linked polymer will usually be the predominant component of the material, typically being present at from 50 weight % to 95 weight % of the total weight of the material, preferably being present from 80 weight % to 95 weight % of the total weight of the material. The binder, in contrast will usually form a much smaller portion of the material, typically being present at from 50 weight % to 1 weight % of the total weight of material, usually being present at from 20 weight % to 1 weight %. Usually, a plasticizer will also be provided in the material, usually within the non-cross-linked phase of the material, and typically being present at from 1 weight % to 20 weight % of the total weight of the material, usually being present at from 3 weight % to 15 weight % of the material. Optionally, the plasticizer may be present in both the non-cross-linked polymer and the cross-linked polymer. Preferred plasticizers include polyethylene glycol, sorbitol, and glycerol.

The polymer which is cross-linked may be a protein, carbohydrate, non-biologic hydrogel-forming polymer or copolymer, or other biologically compatible polymer or combination of polymers which can form a hydrogel. Preferred polymers include proteins, such as gelatin, collagen, albumin, hemoglobin, fibrinogen, fibrin, fibronectin, elastin, keratin, laminin, casein, and the like. Preferred carbohydrate and carbohydrate derivative polymers include glycosaminoglycans, starches, celluloses, hemicelluloses, xylan, agarose, alginate, chitosan, and the like. Exemplary non-biologic hydrogel-forming polymers and copolymers include polyacrylates, polymethacrylates, polyacrylamides, polyvinyl polymers, polylactides-glycolides, polycaprolactones, polyoxyethylenes, and copolymers thereof. Usually, the degree of cross-linking of the cross-linked polymer will be selected to provide a desired swellability within the range set forth above.

The non-cross-linked biologically compatible polymer will usually be a protein or a carbohydrate and may be the same polymer as the polymer which is cross-linked. Exemplary proteins include gelatin, collagen, elastin, albumin, keratin, and the like. Exemplary carbohydrates include glycosaminoglycans, alginate, starch, cellulose, derivatives thereof, and the like. The non-cross-linked polymer may also be non-biological water soluble polymer, such as any of the hydrogel-forming polymers and co-polymers set forth above. A particularly preferred and exemplary hemoactive material according to the present invention comprises a dry matrix of non-cross-linked gelatin polymer and dry cross-linked gelatin polymer present as particles dispersed in the dry gelatin matrix. Such compositions are described in greater detail in the Experimental section hereinafter.

The polymeric compositions of the present invention may comprise combinations of the disrupted, cross-linked polymer hydrogels described above and non-cross-linked polymeric materials, where the disrupted, cross-linked polymeric hydrogels consist of a plurality of subunits having a size determined by preparation method. The size is selected to be useful for packing a confined volume, having both the flowability and the rate of biodegradability described in the Experimental section below. The discrete nature of the cross-linked subunits, however, will leave void areas which may be filled by combination with the non-cross-linked polymeric materials. The non-cross-linked polymeric or other filler material may comprise any of the polymeric materials listed above, and may optionally but not necessarily be the same polymeric material which has been cross-linked to form the cross-linked mechanically disrupted hydrogel. The relative amounts of cross-linked polymer and non-cross-linked polymer may vary, typically having a weight ratio in the range from 20:1 to 1:1 (cross-linked polymer:non-cross-linked polymer), usually in the range from 10:1 to 2:1, preferably from 5:1 to 2:1.

When delivering an active agent, the active agent may be present in either the non-cross-linked polymer or the cross-linked polymer, or both. When present only in the non-cross-linked polymer, the active agent will be released substantially immediately when the material first dissolves upon contact with blood. When present in the non-cross-linked polymer, the material will be released much more gradually, typically over the entire time in which the cross-linked polymer degrades. Optionally, the same or different active agents can be provided in the two different phases of the material in order to provide different controlled release rates of the bioactive agent(s).

The materials of the present invention may be formed as sheets, powders, pellets, plugs, tubes, split tubes, cylinders, or the like, as generally described above. Such forms of the material are preferably produced sterilely (e.g., by aseptic processing) or sterilized and provided in sterile packs as part of kits. In addition to the sterile packs containing the solid forms of the materials, the kits will usually also contain instructions for use setting forth methods for inhibiting bleeding or delivering drugs by placing the sterilized materials at a target site in tissue, e.g., a wound or other site of bleeding tissue.

As a further aspect of the present invention, hemoactive materials may be made by dissolving a non-cross-linked biologically compatible polymer of the types described above in an aqueous medium. Particles of cross-linked biologically compatible polymer as described above are then suspended in the aqueous medium. The aqueous medium is then dried to form a solid phase comprising the dried polymeric particles in a dry matrix of the non-cross-linked polymer. Lyophilization (freeze-drying) is the preferred drying technique, although air drying, heat-assisted drying, spray drying, molding, and other methods could also be used under certain circumstances.

DESCRIPTION OF THE SPECIFIC EMBODIMENTS

Compositions according to the present invention comprise dried hemostatic materials including both a cross-linked biologically compatible polymer and a non-crossed-linked biologically compatible polymer. By "biologically compatible" it is meant that the materials will meet the criteria in standard # ISO 10993-1 (International Organization for Standardization, Geneva, Switzerland). Generally, biologically compatible materials will be free from pyrogenic substances and will not cause adverse biological effects when applied to human tissue according to the methods as described below. Usually, the compositions of the present invention will be resorbable. By "resorbable" it is meant that the compositions will degrade or solubilize when placed directly on to or into a target site in a patient's body over a time period of less than one year, usually from 1 day to 120 days. Usually, the non-cross-linked polymer components of the materials of the present invention will degrade or solubilize much more quickly, typically in several minutes or less. The remaining cross-linked polymer will form a hydrogel at the placement site, where the hydrogel will persist over time, but will be resorbable as just set forth.

Preferred cross-linked polymers according to the present invention are described in detail in co-pending application Ser. No. 09/032,370, filed on Feb. 27, 1998, the full disclosure of which has been previously incorporated herein by reference. The cross-linked biologically compatible polymers may be molecular cross-linked. By "molecular cross-linked", it is meant that the materials comprise polymer molecules (i.e., individual chains) which are attached by bridges composed of either an element, a group, or a compound, where the backbone atoms of the polymer molecules are joined by chemical bonds. Alternatively, the cross-linked polymers may be formed by non-covalent interactions such as ionic or hydrophobic. Cross-linking may be effected in a variety of ways, as will be described in greater detail below.

By "hydrogel," it is meant that the composition comprises a single phase aqueous colloid in which a biologic or non-biologic polymer, as defined in more detail below, absorbs water or an aqueous buffer. Preferably, the hydrogels will have little or no free water, i.e., water cannot be removed from the hydrogel by simple filtration, prior to use.

By "percent swell," it is meant that the dry weight is subtracted from the wet weight, divided by the dry weight and multiplied by 100, where wet weight is measured after the wetting agent has been removed as completely as possible from the exterior of the material, e.g., by filtration, and where dry weight is measured after exposure to an elevated temperature for a time sufficient to evaporate the wetting agent, e.g., 2 hours at 120° C.

"Equilibrium swell" is defined as the percent swell at equilibrium after the polymeric material has been immersed in a wetting agent for a time period sufficient for water content to become constant, typically 18 to 24 hours.

"Target site" is the location to which the hydrogel material is to be delivered. Usually, the target site will be the tissue location of interest, but in some cases the hydrogel may be administered or dispensed to a location near the location of interest, e.g., when the material swells in situ to cover the location of interest.

The cross-linked polymers of the present invention may be formed from biologic and non-biologic polymers. Suitable biologic polymers include proteins, such as gelatin, soluble collagen, albumin, hemoglobin, casein, fibrinogen, fibrin, fibronectin, elastin, keratin, laminin, and derivatives and combinations thereof. Particularly preferred is the use of gelatin or soluble non-fibrillar collagen, more preferably gelatin, and exemplary gelatin formulations are set forth below. Other suitable biologic polymers include polysaccharides, such as glycosaminoglycans (e.g., hyaluronic acid and chondroitin sulfate), starch derivatives, xylan, cellulose derivatives, hemicellulose derivatives, agarose, alginate, chitosan, and derivatives and combinations thereof. Suitable non-biologic polymers will be selected to be degradable by either of two mechanisms, i.e., (1) break down of the polymeric backbone or (2) degradation of side chains which result in aqueous solubility. Exemplary non-biologic hydrogel-forming polymers include synthetics, such as polyacrylates, polymethacrylates, polyacrylamides, polyvinyl resins, polylactides-glycolides, polycaprolactones, polyoxyethylenes, and derivatives and combinations thereof.

The polymer molecules may be cross-linked in any manner suitable to form an aqueous hydrogel according to the present invention. For example, polymeric molecules may be cross-linked using bi- or poly-functional cross-linking agents which covalently attach to two or more polymer molecules chains. Exemplary bifunctional cross-linking agents include aldehydes, epoxies, succinimides, carbodiimides, maleimides, azides, carbonates, isocyanates, divinyl sulfone, alcohols, amines, imidates, anhydrides, halides, silanes, diazoacetate, aziridines, and the like. Alternatively, cross-linking may be achieved by using oxidizers and other agents, such as periodates, which activate side-chains or moieties on the polymer so that they may react with other side-chains or moieties to form the cross-linking bonds. An additional method of cross-linking comprises exposing the polymers to radiation, such as γ-radiation, to activate the side polymer to permit cross-linking reactions. Dehydrothermal cross-linking methods are also suitable. Dehydrothermal cross-linking of gelatin can be achieved by holding it at an elevated temperature, typically 120° C., for a period of at least 8 hours. Increasing the extent of cross-linking, as manifested in a decline in percent swell at equilibrium, can be achieved by elevating the holding temperature, extending the duration of the holding time, or a combination of both. Operating under reduced pressure can accelerate the cross-linking reaction. Preferred methods for cross-linking gelatin molecules are described below.

Exemplary methods for producing molecular cross-linked gelatins are as follows. Gelatin is obtained and placed in an aqueous buffer to form a non-cross-linked hydrogel, typically having a solids content from 1% to 70% by weight, usually from 3% to 10% by weight. The gelatin is cross-linked, typically by exposure to either glutaraldehyde (e.g., 0.01% to 0.05% w/w, overnight at 0° to 15° C. in an aqueous buffer), sodium periodate (e.g., 0.05 M, held at 0° C. to 15° C. for 48 hours) or 1-ethyl-3-(3-dimethylaminopropyl) carbodiimide ("EDC") (e.g., 0.5% to 1.5% w/w, overnight at room temperature), or by exposure to about 0.3 to 3 megarads of gamma or electron beam radiation. Alternatively, gelatin particles can be suspended in an alcohol, preferably methyl alcohol or ethyl alcohol, at a solids content of 1% to 70% by weight, usually 3% to 10% by weight, and cross-linked by exposure to a cross-linking agent, typically glutaraldehyde (e.g., 0.01% to 0.1% w/w, overnight at room temperature). In the case of aldehydes, the pH will usually be held from about 6 to 11, preferably from 7 to 10. When cross-linking with glutaraldehyde, the cross-links appear to be formed via Schiff bases which may be stabilized by subsequent reduction, e.g., by treatment with sodium borohydride. After cross-linking, the resulting granules may be washed in water and optionally rinsed in an alcohol and dried. The resulting cross-linked gelatin may then be used as described in more detail hereinafter. Alternatively, the gelatin may be mechanically disrupted prior to or after cross-linking, also as described in more detail hereinafter.

Exemplary methods for producing molecular cross-linked gelatin compositions having equilibrium percent swells in the range from about 200% to about 5000%, preferably 500% to 1000%, are as follows. Gelatin is obtained and placed in an aqueous buffer (typically at a pH of 6 to 11, preferably at a pH between 7 and 10) containing a cross-linking agent in solution (typically glutaraldehyde, preferably at a concentration of 0.01% to 0.1% w/w) to form a hydrogel, typically having a solids content from 1% to 70% by weight, usually from 3% to 10% by weight. The hydrogel is well mixed and held overnight at 0°–15° C. as cross-linking takes place. It is then rinsed three times with deionized water, optionally rinsed twice with an alcohol (preferably methyl alcohol, ethyl alcohol, or isopropyl alcohol) and allowed to dry at room temperature. Optionally, the hydrogel may be treated with sodium borohydride to further stabilize the cross-linking.

The non-cross-linked biologically compatible polymers may be formed from many of the same polymers described above for the cross-linked components. By using the polymers in a non-cross-linked form, however, the polymers will generally be less persistent in the presence of blood or other aqueous medium and are thus suitable as binders for holding the cross-linked materials of the present invention together. Particularly suitable protein non-cross-linked polymers include gelatin, collagen, elastin, albumin, keratin, and the like. Other suitable non-cross-linked carbohydrate and carbohydrate derivative polymers include glycosaminoglycans, alginate, starch, cellulose, derivatives thereof, and the like. In preparing the compositions of the present invention, the non-cross-linked polymers will typically first be suspended in a suitable medium, typically an aqueous medium, having suitable buffers, secondary binders, plasticizers, preservatives, antioxidants, bioactive agents, or the like, added. Once the non-cross-linked polymer is suspended at a suitable concentration, typically in the range from 0.2 weight % to 10 weight %, preferably from 0.25 weight % to 2 weight %, the cross-linked polymer will be added, typically in a dry particle form. After the dispersion of the cross-linked polymer has been well mixed in the solution of the non-cross-linked polymer, the suspension may be dried by any conventional technique. Preferably, the medium will be spread in a thin layer, typically from 1 mm to 25 mm, depending on the solids concentration in the medium, and lyophilized to produce a dry, sponge-like material which may then be sterilized and used in the methods described hereinbelow. Alternatively, the solution of non-cross-linked polymer, which may also contain other active or bioactive agents, may be sterile filtered and combined in a sterile environment with the cross-linked polymer sterilized by other means and further processing carried out under aseptic conditions. Other suitable drying techniques include air drying, heat drying, spray drying, molding, or the like. While the use of sheet-like materials would be preferred, the materials can be further formed into other geometries, such as pellets, plugs, cylinders, half-cylinders, tubes, or the like, for specific uses. The use of plugs may be preferred in the case of the sealing of vascular tracts, such as percutaneous punctures to a femoral or other artery or vein.

The compositions of the present invention may be further combined with other materials and components, such as bioactive component(s) to be delivered to the patient, viscosity modifiers, such as carbohydrates and alcohols, and other materials intended for other purposes, such as to control the rate of resorption. Exemplary bioactive components include, but are not limited to, proteins, carbohydrates, polysaccharides, nucleic acids, and inorganic and organic biologically active molecules such as enzymes, enzyme inhibitors, antibiotics, antineoplastic agents, bacteriostatic agents, bactericidal agents, antiviral agents, hemostatic agents, local anesthetics, anti-inflammatory agents, hormones, anti-angiogenic agents, antibodies, neurotransmitters, psychoactive drugs, drugs affecting reproductive organs and oligonucleotides, such as antisense oligonucleotides.

Such bioactive components will typically be present at relatively low concentrations, typically below 10% by weight of the compositions, usually below 5% by weight, and often below 1% by weight. Two or more of such active agents may be combined in a single composition and/or two or more compositions may be used to deliver different active components where said components may interact at the delivery site.

Exemplary hemostatic agents include thrombin, fibrinogen and clotting factors. Hemostatic agents like thrombin may be added in concentrations ranging from 50 to 10,000 Units thrombin per gram of the composition (dry weight), preferably from about 100 Units thrombin per gram to about 5000 Units thrombin per gram.

Optionally, the materials of the present invention may include a plasticizer to increase the malleability, flexibility, and rate of solubilization. The plasticizer may be an alcohol, such as polyethylene glycol, sorbitol, or glycerol, preferably being polyethylene glycol having a molecular weight ranging from about 200 to 1000 D, preferably being about 400 D. The plasticizers will be present in the compositions at from about 1% of the solids by weight to 20% of the solids by weight, usually from 3% of the solids by weight to 15% of the solids by weight, of the composition. Usually, the plasticizer will be present at least in the non-cross-linked polymer phase of the material, but may also be present in the cross-linked polymer phase. Conveniently, the plasticizer may be added to the solution of the non-cross-linked polymer which is formed prior to the addition of the cross-linked polymer.

The compositions of the present invention are particularly suitable for inhibiting bleeding (causing hemostasis) on and/or delivering drugs to an abraded or damaged tissue surface, e.g., any organ surface including the liver, spleen, heart, kidney, intestine, blood vessels, vascular organs, and the like. A sheet or other form of the dried material is applied so that the actively bleeding abraded or damaged area is completely covered. Suitable hemostatic agents include thrombin, fibrinogen, and other clotting factors, as described for example in U.S. Pat. Nos. 5,411,885; 4,627,879; 4,265,233; 4,298,598; 4,362,567; 4,377,572; and 4,442,655, the disclosures of which are incorporated herein by reference. Conveniently, catalytic components of the hemostasis agent, e.g., thrombin, may also be added to the compositions of the present invention.

Figure 1:
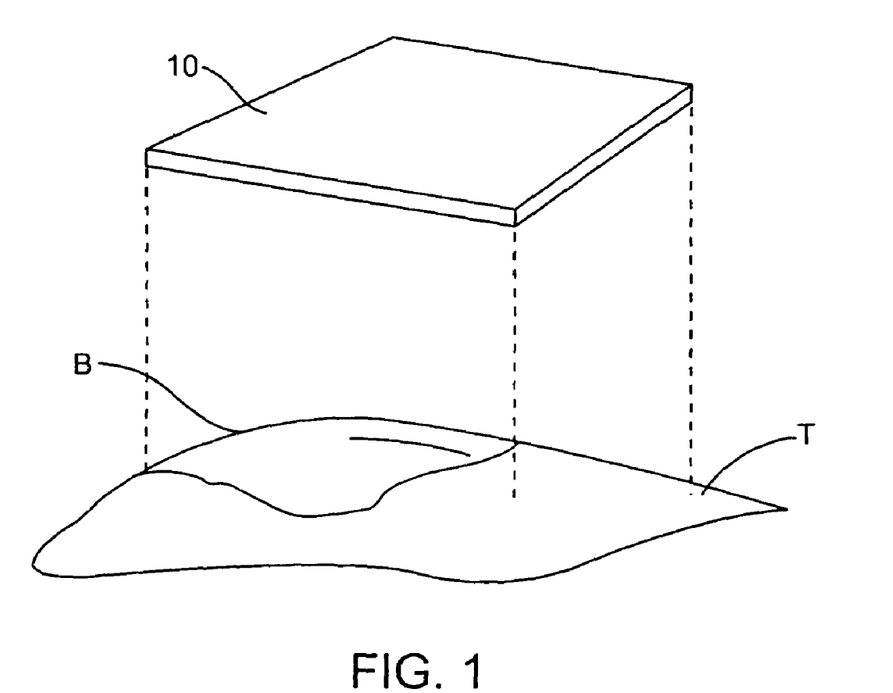
FIG. 1 is a schematic illustration of a sheet of the hemoactive material of the present invention being placed on a bleeding tissue site.
Figure 2:
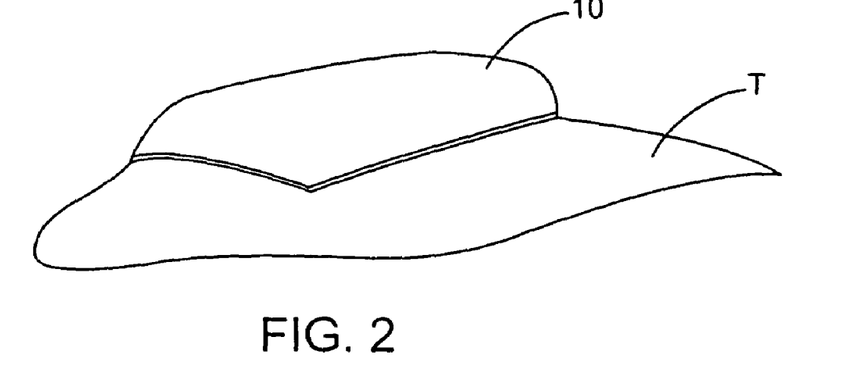
FIG. 2 is a schematic illustration of the bleeding tissue site of FIG. 1 after the material has been placed and a hydrogel formed by the absorption of blood.

Referring now to FIGS. 1 and 2, placement of a sheet 10 of hemoactive material according to the present invention over a bleeding site B and tissue T is illustrated. The sheet 10 may be trimmed to size prior to application and will then be placed over the tissue in its dry form. The sheet will conform to any irregularities in the tissue surface and will immediately begin absorbing water from the blood present at the site. Within minutes, the non-cross-linked polymer component of the material will begin to dissolve and release the cross-linked particles so that they can even more closely conform to the geometry of the site. The cross-linked particles will then begin absorbing water and swelling, as generally shown in FIG. 2. The hemostatic agents, such as thrombin, can be released from the non-cross-linked polymeric component substantially immediately, and over time by the cross-linked component. Substantially complete inhibition of bleeding can be achieved. Optionally, other bioactive agents can be delivered to the site using the same sheet of material.

Figure 3:
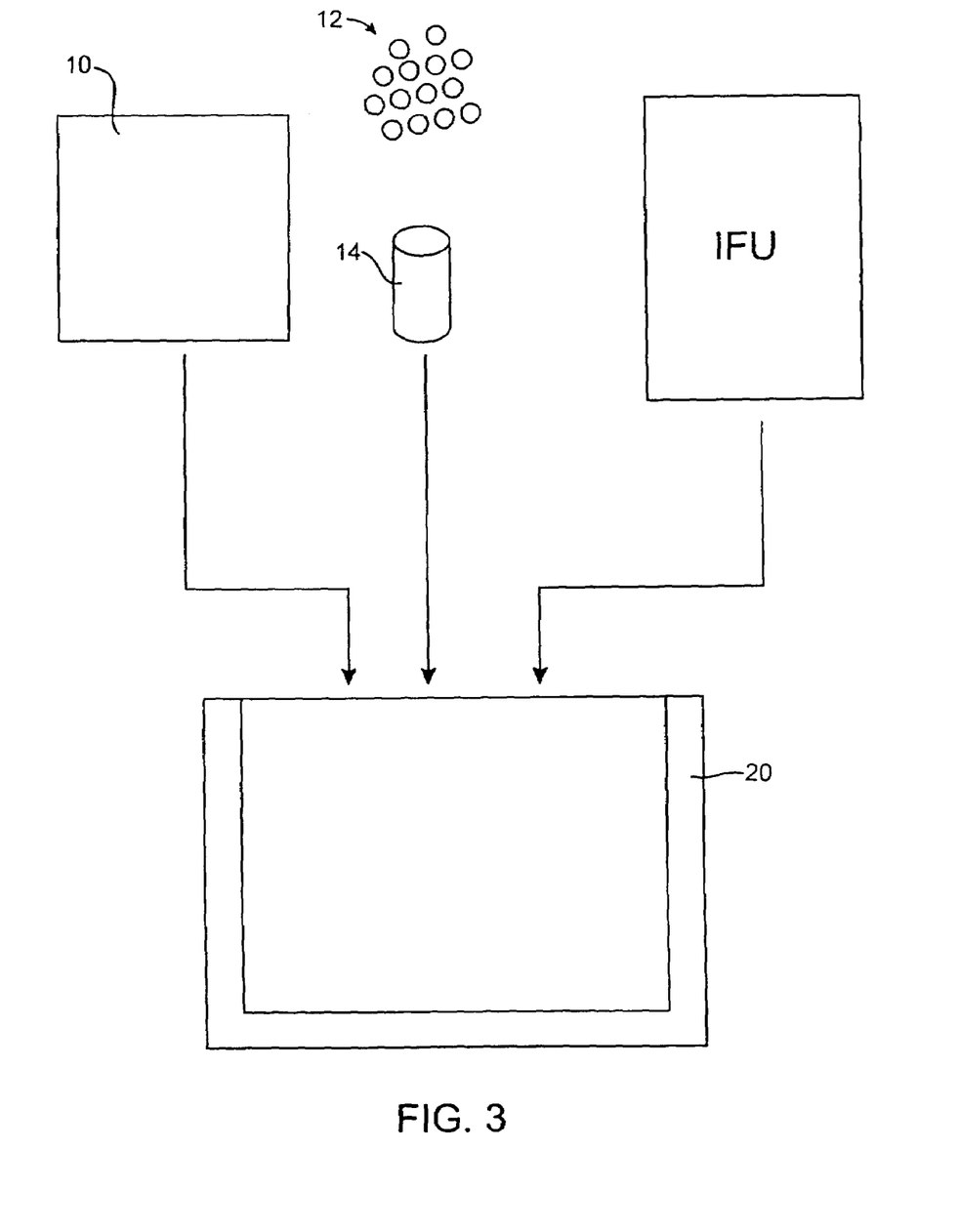
FIG. 3 is a schematic illustration of kits according to the present invention comprising various forms of the hemoactive material, instructions for use, and packaging.

Referring now to FIG. 3, kits according to the present invention will comprise a sheet 10 or other form of the dried polymeric material of the present invention, such as pellets 12, plugs 14, or the like. The materials will be formed sterilely or will be sterilized, preferably by terminal sterilization using $\gamma$-irradiation, ethylene oxide, electronic beam irradiation, and the like. While still in a sterile form, the materials will be packaged in a sterile package 20, such as a pouch, tube, tray, box, or the like. Instructions for use setting forth a method of placing the material over tissue in the presence of blood, e.g., at a wound, or surgical site, will also be provided as part of the kit.

The following examples are offered by way of illustration, not by way of limitation.

EXPERIMENTAL

EXAMPLE 1

Materials and Methods for Production of Uncross-Linked Gelatin Powder

Bovine corium (Spears Co. PA) was agitated in an aqueous sodium hydroxide (Spectrum Chemical Co., CA) solution (0.1 M to 1.5 M preferably 0.4 M to 1.2 M) for a period of 1 to 18 hours (preferably one to four hours) at a temperature of 2°C. to 30° C. (preferably 22° C. to 30° C). The corium slurry was then neutralized using an inorganic acid such as hydrochloric acid, phosphoric acid or sulfuric acid (Spectrum Chemical Co., CA) and the neutralized liquid phase was then separated from the insoluble corium by filtration through a sieve. The corium was then washed with non-pyrogenic water and an alcohol such as isopropyl alcohol (Spectrum Chemical Co., CA). After 3 to 12 washes, the corium was suspended in non-pyrogenic water and the corium/water slurry may be then heated to 50° C. to 90° C. preferably 60° C. to 80° C. to thermally gelatinize the corium. During the gelatinization cycle, the pH of the corium/water slurry was adjusted and controlled from pH 3 to pH 11, preferably pH 6 to pH 9. Also, the insoluble corium in the slurry may be disrupted by agitation and/or homogenization. The disruption can occur before, during, or after the thermal gelatinization cycle. Thermal gelatinization was conducted for one to six hours. After gelatinization, the slurry was clarified. The gelatin slurry was dewatered by drying at 15° C. to 40° C., preferably 20° C. to 35° C. The dry gelatin, where dry implies a moisture content less than 20% by weight, was then disrupted by grinding.

EXAMPLE 2

Materials and Methods for Production of Lyophilized Composite Mixture of Cross-Linked and Uncross-Linked Biopolymer in Sheet Form Uncross-linked gelatin powder was produced from bovine corium (Spears Co., PA) as in Example 1. A portion of the gelatin was used to make cross-linked gelatin particles, approximately 0.02 mm to 1.5 mm in diameter, by suspending the gelatin powder at 2.0% to 4.0% solids by weight in an aqueous solution at a pH between 7 and 10 containing 0.0025% to 0.075% by weight glutaraldehyde for 18 to 24 hours at 5° C. to 15° C. The solids were separated from the suspending buffer by sedimentation or filtration, rinsed with water, and re-suspended in a solution of sodium borohydride, 0.00833% to 0.0667% by weight, at a pH between 7 and 12, preferably 7 to 9. After one to six hours, the resulting cross-linked gelatin particles were separated from the aqueous phase by filtration or sedimentation, rinsed with water, and dried at ambient temperature.

A 30 mL solution was produced containing (by weight) 0.1% to 2.0% non-cross-linked gelatin powder, 0.1% to 2.0% polyethylene glycol (Spectrum Chemical, Gardena, Calif.) of an average molecular weight of 400 D, and 5,000 units to 10,000 units of bovine thrombin (Gentrac, Inc., Middleton, Wis.) in deionized water or buffer containing ascorbate. 1.0 g to 4.0 g of cross-linked gelatin particles were added to this solution and suspended. About 25 to 30 g of the resulting suspension were poured into a metal dish, approximately 7.5 cm in diameter, which was then placed in a bath of alcohol and dry ice for 5 to 10 minutes. The dish and its contents were next held for about one hour at −40° C. and then placed in a lyophilization jar and transferred to a Labconco freeze drying unit, where lyophilization was allowed to proceed for 18 hours. At the end of the lyophilization, the dish contained a flexible, spongy, slightly brittle solid disc of a composite material, about 2 mm to 8 mm thick, comprised of cross-linked gelatin particles held within a matrix of non-cross-linked gelatin and other additives. The composite material was stored in a sealed plastic bag at room temperature until used or transferred to a Chex-All pouch (Propper, Long Island City, N.Y.) for shipment to be γ-irradiated.

EXAMPLE 3

Use of Lyophilized Composite Material as a Hemostatic Agent

Heparin was administered intravenously to a farm grade Hampshire/Yorkshire cross pig (Pork Power Farms, Turlock, Calif.) to prolong the activated clotting time (ACT) of the animal to approximately three to five times its baseline value. A shallow circular divot, approximately 1 cm in diameter, was surgically produced on the spleen of the pig to test the hemostatic efficacy of the lyophilized composite material. The resulting lesion bled freely. A piece of the lyophilized composite material, prepared as in Example 2 and approximately 2.0 cm×3.0 cm in size, was applied to the lesion with compression for two minutes. After compression was removed, no bleeding was observed. Three minutes later, some slight re-bleeding occurred in areas not fully contacted with the material. Additional material was applied with compression for one minute. After compression was removed, no further bleeding was observed. The lesion appeared to be sealed with a mixture of clotted blood and the applied composite material.

EXAMPLE 4

Use of Lyophilized Composite Material as a Hemostatic Agent

A shallow divot, approximately 1 cm×1 cm, was surgically created on the liver of a farm grade Hampshire/Yorkshire cross pig (Pork Power Farms, Turlock, Calif.) to test the hemostatic efficacy of the lyophilized composite material. The resulting lesion bled freely. A 2 cm×3 cm piece of lyophilized composite material, prepared as in Example 2, was applied to the lesion with compression for one minute. After compression was removed, no bleeding was observed. The lesion appeared to be sealed with a mixture of clotted blood and the applied composite material.

EXAMPLE 5

Use of Lyophilized Composite Material as a Hemostatic Agent

Heparin was administered intravenously to a farm grade Hampshire/Yorkshire cross pig (Pork Power Farms, Turlock, Calif.) to prolong the activated clotting time (ACT) of the animal to approximately three to five times its baseline value. A shallow divot, approximately 1 cm×1 cm, was then surgically created on the liver to test the hemostatic efficacy of the lyophilized composite material. The resulting lesion bled freely. A 2 cm×3 cm piece of lyophilized composite material, prepared as in Example 2, was applied to the lesion with compression for one minute. After compression was removed, no bleeding was observed from the site. The lesion appeared to be sealed with a mixture of clotted blood and the applied composite material.

EXAMPLE 6

Irradiation of the Lyophilized Composite Material

Sheets of lyophilized composite material were produced as in Example 2, sealed into Chex-All pouches (Propper, Long Island City, N.Y.), and subjected to γ-irradiation at 25–40 kGy (2.5–4.0 MRad) (a typical sterilizing dose) at ambient temperature (Sterigenics, Hayward, Calif.).

EXAMPLE 7

Use of the Irradiated Material as a Hemostatic Agent

Heparin was administered intravenously to a farm grade pig to prolong the activated clotting time (ACT) of the animal to approximately three to five times its baseline value. A shallow trough, approximately 2 cm×0.5 cm, was surgically created on the liver of the pig to test the hemostatic efficacy of the material produced in Example 6. The resulting lesion bled freely. A 3 cm×0.5 cm piece of material produced in Example 6 was applied to the lesion with compression for two minutes. After compression was removed, no bleeding was observed. The lesion appeared to be sealed with a mixture of clotted blood and the applied composite material. Twenty minutes after application, excess material was removed from the site with forceps. This did not disturb the seal and no subsequent bleeding was observed.

EXAMPLE 8

Use of the Irradiated Material as a Hemostatic Agent

Heparin was administered intravenously to a farm grade pig to prolong the activated clotting time (ACT) of the animal to approximately three to five times its baseline value. A hole, approximately 1.0 cm in diameter, was surgically created completely through the liver of the pig to test the hemostatic efficacy of the material produced in Example 6. The resulting lesion bled freely. A strip of the material produced in Example 6, approximately 0.5 cm×3.0 cm in size, was folded and placed into the lesion as a pledget and held in place with compression for about two minutes. After compression was released, no bleeding was observed.

Following irrigation with saline, no further bleeding was observed. The lesion appeared to be sealed with a mixture of clotted blood and the applied composite material.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A dried hemoactive material for inhibiting bleeding or delivering an agent, comprising:
    a cross-linked biologically compatible polymer which forms a hydrogel when exposed to blood; and
    a non-cross-linked biologically compatible polymer which solubilizes when exposed to blood:
    wherein the cross-linked polymer is dispersed in a dried matrix of the non-cross-linked polymer.

2. A material as in claim 1, wherein the cross-linked polymer is a protein selected from the group consisting of gelatin, collagen, albumin, hemoglobin, fibrinogen, fibrin, fibronectin, elastin, keratin, laminin, and casein.

3. A material as in claim 1, wherein the cross-linked polymer is a carbohydrate or carbohydrate derivative selected from the group consisting of glycosaminglycans, starches, celluloses, hemicelluloses, xylan, agarose, alginate, and chitosan.

4. A material as in claim 1, wherein the cross-linked polymer is a non-biologic hydrogel-forming polymer or copolymer selected from the group consisting of polyacrylates, polymethacrylates, polyacrylamides, polyvinyl polymers, polylactides-glycolides, polycaprolactones, polyoxyethelenes, and copolymers thereof.

5. A material as in claim 1, wherein the non-cross-linked biologically compatible polymer is a protein selected from the group consisting of gelatin, collagen, albumin, elastin, and keratin.

6. A material as in claim 1, wherein the non-cross-linked biologically compatible polymer is a carbohydrate or carbohydrate derivative selected from the group consisting of glycosaminoglycans, alginate, starch, cellulose, and derivatives thereof.

7. A dried hemoactive material for inhibiting bleeding or delivering an agent, comprising:
    a non-cross-linked polymer comprising a dry gelatin matrix; and
    dry, cross-linked gelatin polymer particles dispersed in the dry non-cross-linked gelatin matrix.

8. A material as in claim 1 or 7, wherein the cross-linked polymer has a degradation time of at least one day.

9. A material as in claim 1 or 7, wherein the non-cross-linked polymer solubilizes in 15 minutes or less when exposed to blood.

10. A material as in claim 1 or 7, wherein the cross-linked polymer is fragmented so that, upon hydration in blood, the polymer will form a gel with a sub-unit size in the range from 0.01 mm to 5 mm.

11. A material as in claim 10, wherein the cross-linked polymer has an equilibrium swell in the range from 400% to 5,000%.

12. A material as in claim 1 or 7, in the form of a sheet having a thickness in the range from 1 mm to 75 mm.

13. A material as in claim 12, wherein the sheet is packed in a sterile pack.

14. A kit comprising:
    a sterile pack; a sterile sheet of material as in claim 12, packaged in the sterile pack; and
    instructions for use setting forth a method for inhibiting bleeding by placing the sterilized sheet of material over bleeding tissue.

15. A material as in claim 1 or 7, wherein the cross-linked polymer is present at from 50 weight % to 95 weight % of the material and the non-cross-linked material is present at from 50 weight % to 1 weight % of the material.

16. A material as in claim 15, further comprising a plasticizer present at from 1 weight % to 20 weight % of the material.

17. A material as in claim 16, wherein the plasticizer is present in at least the non-cross-linked polymer.

18. A material as in claim 17, wherein the plasticizer is selected from the group consisting of polyethylene glycol, sorbitol, and glycerol.

19. A material as in claim 1 or 7, further comprising an active agent.

20. A material as in claim 19, wherein the active agent is present in at least the non-cross-linked polymer.

21. A material as in claim 19, wherein the active agent is present in at least the cross-linked polymer.

22. A material as in claim 19, wherein the active agent is present in both the non-cross-linked polymer and the cross-linked polymer.

23. A material as in claim 19, wherein the active agent is selected from the group consisting of antibiotics, antineoplastic agents, bacteriostatic agents, bactericidal agents, antiviral agents, anesthetics, anti-inflammatory agents, hormones, anti-angiogenic agents, antibodies, enzymes, enzyme inhibitors, and neurotransmitters.

24. A method for delivering an active agent to a patient, said method comprising:
    applying the material of claim 19 to or near a target region of the patient.

25. A material as in claim 19, wherein the active agent is a hemostatic substance.

26. A method for inhibiting bleeding, said method comprising:
    applying the material of claim 25 to a wound site.

27. A material as in claim 25, wherein the hemostatic substance is a clotting factor.

28. A material as in claim 27, wherein the clotting factor is thrombin.

29. A method for making a hemoactive material, said method comprising:
    dissolving in an aqueous medium a non-cross-linked biologically compatible polymer which solubilizes when exposed to blood;
    suspending in said aqueous medium containing the non-cross-linked polymer a cross-linked biologically compatible polymer which forms a hydrogel when exposed to blood; and
    drying the resulting aqueous medium containing both polymers to form a solid phase comprising the cross-linked polymer in dry form dispersed in a dry matrix of the non-cross-linked polymer.

* * * * *